US00PP08230P

United States Patent [19]

Olesen et al.

[11] Patent Number: Plant 8,230

[45] Date of Patent: May 18, 1993

[54] ROSE PLANT—POULBERO VARIETY

[75] Inventors: Mogens Olesen; Pernille Olesen, both of Fredensborg, Denmark

[73] Assignee: The Conard-Pyle Company, West Grove, Pa.

[21] Appl. No.: 779,995

[22] Filed: Oct. 21, 1991

[51] Int. Cl.[5] ..... A01H 5/00

[52] U.S. Cl. ..... Plt./11

[58] Field of Search ..... Plt./11, 12, 13, 22

*Primary Examiner*—Howard J. Locker

*Attorney, Agent, or Firm*—Burns, Doane, Swecker & Mathis

[57] ABSTRACT

A new and distinct variety of Grandiflora rose plant is provided which continuously and abundantly forms fully double long lasting blossoms bearing an attractive combination of red, orange, yellow, and pink tones. The vegetation is very vigorous and the plant exhibits an upright and bushy growth habit. Good winter hardiness and above-average resistance to diseases have been observed. The new variety is particularly well suited for service as attractive ornamentation in parks and gardens.

1 Drawing Sheet

SUMMARY OF THE INVENTION

The new variety of Grandiflora rose plant was created by artificial pollination wherein two parents were crossed which previously had been studied in the hope that they would contribute the desired characteristics. The female parent (i.e., the seed parent) of the new variety was the Berolina variety (nonpatented in the United States). The male parent (i.e., the pollen parent) was an unnamed seedling (nonpatented in the United States). The parentage of the new variety can be summarized as follows:

Berolina × Unnamed Seedling.

The seeds resulting from the above pollination were sown and small plants were obtained which were physically and biologically different from each other. Selective study resulted in the identification of a single plant of the new variety.

It was found that the new variety of Grandiflora rose plant of the present invention possesses the following combination of characteristics:

(a) forms in abundance on a continuous basis attractive long-lasting fully double blossoms which exhibit brilliant coloration comprising a combination of red, orange, yellow, and pink tones,
(b) exhibits vigorous vegetation,
(c) exhibits an upright and bushy growth habit,
(d) exhibits good winter hardiness,
(e) exhibits above-average resistance to diseases, and
(f) is particularly suited for growing in parks and gardens.

The new variety well meets the needs of the horticultural industry and forms attractive ornamentation in the landscape.

The new variety has been found to undergo asexual propagation by a number of routes at West Grove, Pa., including budding, grafting, cuttage, etc. The characteristics of the new variety have been found to be stable and to be strictly transmissible by such asexual propagation from one generation to another.

The new variety has been named the Poulbero variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during September while budded on *Rosa froebelli* understock when grown outdoors at West Grove, Pa.

Character a — designates a specimen of flowering stem;
Character b — designates another specimen of a flowering stem;
Character c — designates a specimen of a young shoot;
Character d — designates a specimen of a floral bud before the opening of the sepals;
Character e — designates a specimen of a floral bud at the opening of the sepals;
Character f — designates a specimen of a floral bud at the opening of the petals;
Character g — designates a specimen of a flower in the course of opening;
Character h — designates a specimen of another flower in the course of opening;
Character i — designates a specimen of a floral receptacle showing the arrangement of the stamens and pistils;
Character j — designates a specimen of a floral receptacle showing the arrangement of the pistils (stamens removed);
Character k — designates a specimen of an open flower — plan view — obverse;
Character l — designates a specimen of an open flower — plan view — reverse;
Character m — designates a specimen of a fully open flower — plan view — obverse;
Character n — designates a specimen of a fully open flower — plan view — reverse;
Character o — designates a specimen of a main branch;
Character p — designates specimens of leaves with three leaflets — plan view — upper surface (top), and lower surface (bottom);

Character q — designates specimens of leaves with five leaflets — plan view — upper surface (top), and lower surface (bottom); and Character r — designates a leaf with seven leaflets — plan view — upper surface.

DETAILED DESCRIPTION

The chart used in the identification of the colors is that of The Royal Horticultural Society (R.H.S. Colour Chart). The description is based on the observation of two-year old plants made during September while budded on *Rosa froebelli* understock and growing outdoors at West Grove, Pa. The coloration in common terms sometimes precedes reference to the chart.

Class: Grandiflora.

Plant:

*Height.*—Approximately 45 to 50 inches.

*Width.*—Approximately 40 inches.

*Habit.*—Upright and bushy.

Branches:

*Color.*—Young stems: Yellow-Green Group 144C stained with reddish coloration. Adult wood: lettuce green, Yellow-Green Group 144A.

*Thorns.*—Size: medium. Quantity: low to moderate; however, there are also numerous small prickles. Color: reddish yellow green on young stems, and tan with a purplish-red base and tip.

Leaves:

*Stipules.*—Adnate, pectinate, fairly narrow and linear.

*Petioles.*—Length: approximately 3 cm. on average on a mature leaf.

*Petioles.*—Upper surface: reddish green on young foliage and medium green on mature foliage. Under surface: reddish green on young foliage and medium green on mature leaves with numerous tiny reddish prickles.

*Leaflets.*—Number: 3, 5 (most often), and rarely 7. Shape: oval spear-shaped. Serration: simple and regular. Texture: leathery. General appearance: fairly ample and dense, semi-matte foliage. Color (young foliage): Upper surface: Greyed-Purple Group 187A. Under surface: Greyed-Purple Group 183D. Color (adult foliage): Upper surface: Yellow-Green Group 147A turning to Yellow-Green Group 147B on older leaves. Under surface: Yellow-Green Group 148B stained with reddish coloration towards the outside and between the veins, and turning to Yellow-Green Group 148C on the older leaves.

Inflorescence:

*Number of flowers.*—Commonly 1 to 10 fully double blooms per stem, and most frequently 3 to 7 of such blooms per stem.

*Peduncle.*—Length: approximately 6 to 7 cm. on average. Color: reddish-green turning to light green on older blooms.

*Sepals.*—Upper surface: tomentose, greenish in coloration. Under surface: light green, largely maculated with reddish coloration, the outer sepals have appendiculated edges.

*Buds.*—Shape: elongated. Length: approximately 4 cm. on average. Size: large. Color (upon opening): Upper surface: currant red, Red Group 46A near the top and edges of the petals, Red Group 46B towards the middle of the petals, and Green-Yellow Group 1B near the point of attachment.

Under surface: currant red, Red Group 46A near the top and edges of the petals, turning progressively to Red Group 46D towards the middle of the petals, and Green-Yellow Group 1B near the point of attachment.

*Flower.*—Shape: cup-like. Diameter: approximately 11 to 12 cm. when fully open. Color (when opening begins): Upper surface: Dutch vermilion, Red Group 40A, strongly suffused with light crimson, Red Group 52A, near the tip of the petals especially on the outer petals, and turning to bright Yellow-Orange Group 14A near the point of attachment. Under surface: on the outer petals Red Group 51A on the outer edges progressively changing to Red Group 51D, then to Red Group 40D, and finally to Yellow-Orange Group 14A near the point of attachment; and on the inner petals Yellow-Orange Group 14A at the point of attachment turning to Yellow-Orange Group 14B suffused with Red Group 40B which intensifies towards the edges with the edges being Red Group 40A suffused with Red Group 40B. Color (when blooming): Upper surface: Red Group 40B somewhat suffused with Red Group 41B near the edges and Yellow-Orange Group 14C changing to Yellow-Orange Group 14A near the point of attachment. Under surface: on the outer petals Red Group 47D suffused with Red Group 40C turning progressively to Yellow-Orange Group 14B and then to Yellow-Orange Group 14A at the point of attachment; and on the inner petals Red Group 40C suffused with Yellow-Orange Group 14B changing to Yellow-Orange Group 14A near the point of attachment. Color (at end of opening): Upper surface: Red Group 47B strongly suffused with Red Group 40D and changing to Yellow-Orange Group 14B and ultimately to Yellow-Orange Group 14C near the point of attachment. Under surface: Red Group 47D strongly suffused with Red Group 40D, changing to Yellow-Orange Group 14D and ultimately to Yellow-Orange Group 14C near the point of attachment. Fragrance: light and spicy. Lasting quality: long. Petal number: approximately 20 to 23 on average with a few petaloids at the center. Petal shape: the outer petals are rounded, and the inner petals are more or less indented. Texture: very consistent. Petal drop: good. Stamen number: approximately 130 to 165 on average. Anthers: straw-like coloration changing to black when mature. Filaments: very pure straw-like coloration turning to almost white near the top when mature, fairly uniform in height, and located substantially uniformly in a circle having a radius of approximately 5 mm. in a spaced relationship about a cluster of pistils in the center. Pistils: approximately 92 to 95 on average. Stigmas: normal, reddish in coloration, and turning to a straw-like coloration near the top. Styles: normal, twisted and commingled, irregular in height. Receptacle: light green, at the dehiscence of the anthers in longitudinal section it is fairly narrow and in the shape of a funnel, and is tomentose in the area between the pistils and stamens.

Development:

*Vegetation.*—Vigorous.

*Blooming.*—Continuous from June to early frost.
*Aptitude to bear fruits.*—Poor.
*Resistance to frost.*—Very good.
*Resistance to diseaes.*—Above average.

We claim:

1. A new and distinct variety of Grandiflora rose plant characterized by the following combination of characteristics:

(a) forms in abundance on a continuous basis attractive long-lasting fully double blossoms which exhibit brilliant coloration comprising a combination of red, orange, yellow, and pink tones,
(b) exhibits vigorous vegetation,
(c) exhibits an upright and bushy growth habit,
(d) exhibits good winter hardiness,
(e) exhibits above-average resistance to diseases, and
(f) is particularly suited for growing in parks and gardens;

substantially as herein shown and described.

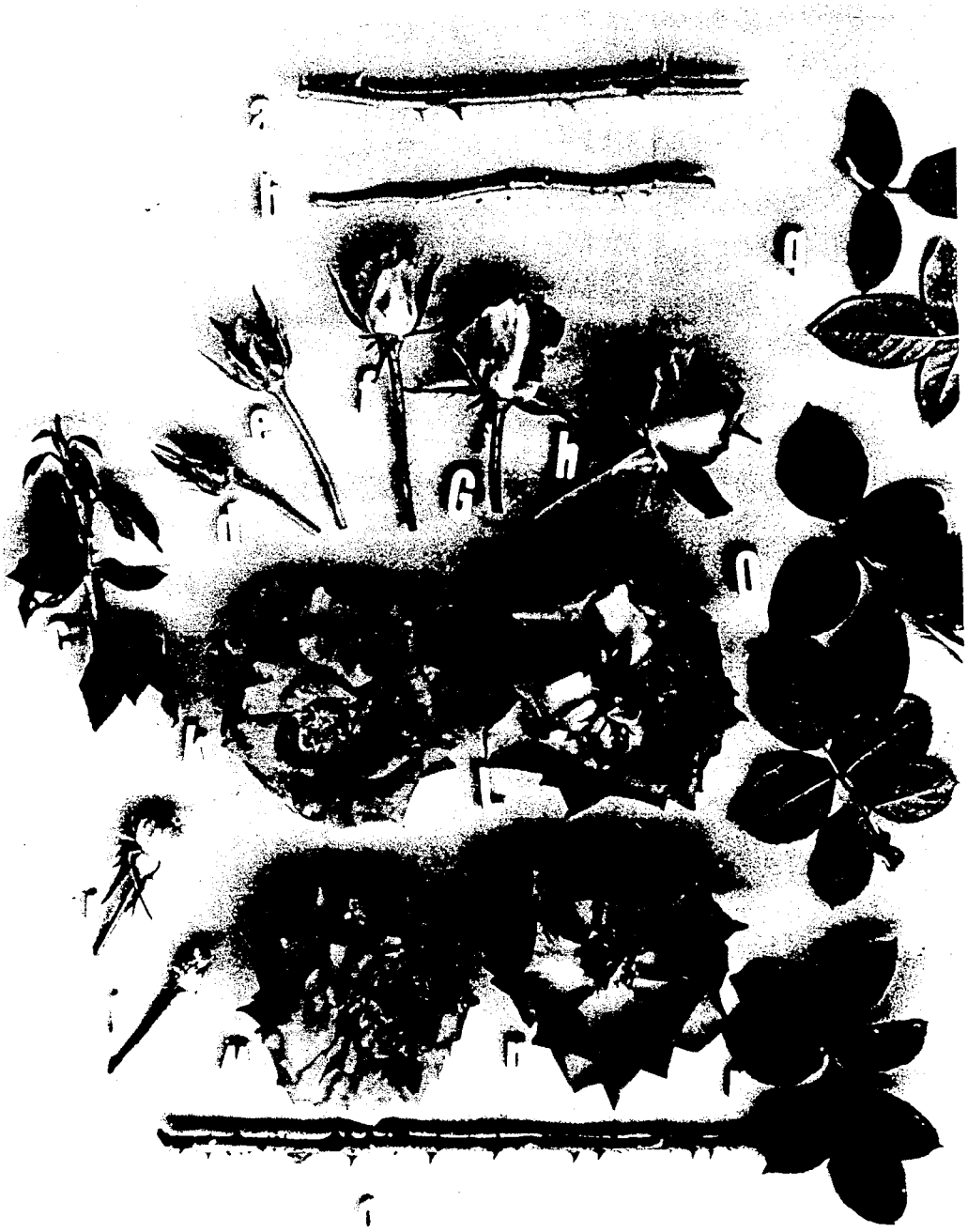

* * * * *